United States Patent [19]

Plummer

[11] Patent Number: 4,487,778
[45] Date of Patent: Dec. 11, 1984

[54] INSECTICIDAL ESTERS DERIVED FROM BENZOCYCLOALKANE-THIO-PHENEMETHYL COMPOUNDS

[75] Inventor: Ernest L. Plummer, Yardley, Pa.

[73] Assignee: FMC Corporation, Philadelphia, Pa.

[21] Appl. No.: 461,420

[22] Filed: Jan. 27, 1983

[51] Int. Cl.$^3$ .................... A01N 43/12; A01N 53/00; C07D 333/80
[52] U.S. Cl. .................... 424/275; 424/258; 424/263; 424/285; 546/93; 546/101; 546/111; 549/43; 549/458
[58] Field of Search .......................... 549/43; 424/275

[56] References Cited

U.S. PATENT DOCUMENTS

| 3,679,667 | 7/1972 | Fanta | 260/240 R |
| 3,922,269 | 11/1975 | Elliott et al. | 260/347.4 |
| 4,024,163 | 5/1977 | Elliott et al. | 260/347.4 |
| 4,179,575 | 12/1979 | Martel et al. | 562/506 |
| 4,231,932 | 11/1980 | Martel et al. | 260/326 A |
| 4,329,518 | 5/1982 | Plummer | 568/807 |
| 4,339,457 | 7/1982 | Plummer et al. | 424/274 |

OTHER PUBLICATIONS

Adams, et al., *J. Am. Chem. Soc.*, 42, 599, (1920).
Beaven, et al., *J. Chem. Soc.*, 2708, (1955).
Brown, et al., *Adv. Pestic. Sci., Plenary Lect. Symp. Paper Int. Congr. Pestic. Chem.*, 4th, 1978, 2, p. 190.
Burness, D. M., *Org. Synth.*, Coll. vol. 4, 628, (1963).
Cadogan, J., *J. Chem. Soc.*, 4257, (1962).
Clarke, et al., *J. C. S. Perkin I*, 2956, (1973).
Cope, et al., *J. Am. Chem. Soc.*, 78, 1012, (1956).
Davis, et al., "Synthetic Pyrethroids," ACS Symposium Series No. 42, Washington, D.C., 1977, p. 37.
Elliott, et al., *Abstracts, Fourth International Congress of Pesticide Chemistry*, Zurich, 1978.
Elliott, et al., *Chem. Soc. Rev.*, 7, 473, (1978).
Elliott, et al., *Pestic. Sci.*, 7, 499, (1976).
Farkas, et al., *Coll. Czech. Chem. Comm.*, 25, 1815, (1960).
Grovenstein, et al., *J. Am. Chem. Soc.*, 89, 2348, (1967).
Henrick, et al., *Pestic. Sci.*, 11, 224, (1980).
Holan, et al., *Nature*, 272, 734, (1978).
Johnson, et al., *J. Am. Chem. Soc.*, 71, 1092, (1949).
Kitahara, et al., *Agr. Biol. Chem.*, 38, 1511, (1974).
Lindsay, et al., *J. Am. Chem. Soc.*, 83, 943, (1961).
Matsui, et al., *Agr. Biol. Chem.*, 28, 27, (1964).
Matsui, et al., *Agr. Biol. Chem.*, 31, 1143, (1967).
Miyakado, et al., *Agr. Biol. Chem.*, 39, 267, (1975).
Ohno, et al., *Agr. Biol. Chem.*, 38, 881, (1974).
Szeja, W., *Synthesis*, 822, (1979).

*Primary Examiner*—Richard L. Raymond
*Attorney, Agent, or Firm*—R. L. Hansen; H. R. Ertelt

[57] ABSTRACT

Certain benzocycloalkaneheteroaromaticmethyl, e.g., benzocycloalkanethiophenemethyl, esters and insecticidal compositions containing these esters are useful for the control of a broad range of insects and acarids.

9 Claims, No Drawings

INSECTICIDAL ESTERS DERIVED FROM BENZOCYCLOALKANE-THIOPHENEMETHYL COMPOUNDS

This invention pertains to the field of bioaffecting compositions; more specifically, it pertains to novel carboxylic acid esters which are pyrethroid insecticides, processes and intermediates thereto, insecticidal and acaricidal compositions containing the novel esters, and to the use of the compositions for controlling insects and acarids.

Pyrethrins have long been of interest as insecticides. Ever since it was discovered that pyrethrins are organic esters, various synthetic modifications have been made in the carboxylic acid and in the alcohol moieties on either side of the ester linkage. Many of the synthetic pyrethroids are more effective than the natural pyrethrins, and recent modifications have overcome a chronic pyrethrin problem—instability to air and light.

The carboxylic acid moiety in the aforesaid esters is often a 2,2-dimethylcyclopropane-1-carboxylic acid with various substituents in the 3-position. Many variations in the alcohol moiety of the aforesaid esters have been investigated also. U.S. Pat. No. 4,329,518 discloses that various [1,1'-biphenyl]-3-ylmethanols give insecticidal esters when coupled with appropriate acids. The alcohol may be heterocyclic, e.g., 5-benzyl-3-furylmethyl alcohol or 2-methyl-3-(pyrrol-1-yl)phenylmethanol. The latter is disclosed in U.S. Pat. No. 4,339,457. The structural features of pyrethroid insecticides have been reviewed, e.g., *Chem. Soc. Rev.*, 7, 473 (1978).

It has now been found that insecticidal and acaricidal esters result when a benzocycloalkaneheteroaromaticmethyl moiety is coupled with a pyrethroid carboxylic acid moiety. Like the earlier esters, several of the new esters are capable of both geometrical and optical isomerism, the biological activity varying somewhat according to the specific isomer. The terms "benzenecycloalkaneheteroaromaticmethyl ester" or "benzocycloalkane-thiophenemethyl ester" employed herein are intended to include generically all optical and geometrical isomers of the named compound and mixtures thereof. The terms "halo," "halogen," or "halide" mean fluorine, chlorine or bromine. The term "lower" modifying alkyl or alkoxy means $C_1$ to $C_6$, preferably $C_1$ to $C_4$.

Insecticidal and acaricidal benzocycloalkaneheteroaromaticmethyl esters of this invention are represented by Formula I

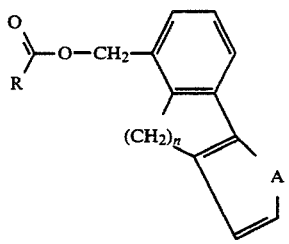

I wherein A is —S—, —O—, or —N═CH—, n is 1-4, and R is a pyrethroid acid residue, i.e., the residue of a carboxylic acid which forms an insecticidal ester with 3-phenoxybenzyl alcohol.

Attractive pyrethroid acid residues include 3-(2,2-dihaloethenyl)-2,2-dimethylcyclopropyl, especially 3-(2,2-dichloroethenyl)-2,2-dimethylcyclopropyl; 3-(cyclopentylidenemethyl)-2,2-dimethylcyclopropyl; 3-(2-methyl-1-propenyl)-2,2-dimethylcyclopropyl; 3-(1,2-dibromo-2,2-dichloroethyl)-2,2-dimethylcyclopropyl; 3-(1,2,2,2-tetrabromoethyl)-2,2-dimethylcyclopropyl; 3-(2-chloro-3,3,3-trifluoro-1-propenyl)-2,2-dimethylcyclopropyl; 3-(3-chloro-2,3,3-trifluoro-1-propenyl)-2,2-dimethylcyclopropyl; 3-(2,3-dichloro-3,3-difluoro-1-propenyl)-2,2-dimethylcyclopropyl; 2,2,3,3-tetramethylcyclopropyl; 2,2-dichloro-3,3-dimethylcyclopropyl; 4-chloro-α-(1-methylethyl)phenylmethyl; 4-difluoromethoxy-α-(1-methylethyl)phenylmethyl; 3-(1,3-butadienyl)-2,2-dimethylcyclopropyl; 2,2-dimethyl-3-(oximinomethyl)cyclopropyl; 2-(2-chloro-α,α,α-trifluoro-p-toluidino)-3-methylbutyl; 3-(2,3,4,5-tetrahydro-2-oxothien-3-ylidenemethyl)-2,2-dimethylcyclopropyl; 2,2-dichloro-1-(4-ethoxyphenyl)cyclopropyl; 4-halo-α-(1-cyclopropyl)phenylmethyl; spiro[2,2-dimethylcyclopropane-1,1'-[1H]-indene]-3-yl; spiro[3-(2,2-dichloroethenyl)cyclopropane-1,1'-cyclohexane]-2-yl; spiro[3-(2,2-dichloroethenyl)cyclopropane-1,1'-cyclobutane]-2-yl; 3-phenyl-2,2-dimethylcyclopropyl; 3-(4-halophenyl)-2,2-dimethylcyclopropyl; 3-(4-methoxyphenyl)-2,2-dimethylcyclopropyl; 3-(4-ethoxyphenyl)-2,2-dimethylcyclopropyl; and 3-(3,4-methylenedioxyphenyl)-2,2-dimethylcyclopropyl.

Among the aforesaid benzocycloalkaneheteroaromaticmethyl esters it is preferred that A be —S—, i.e., benzocycloalkanethiophenemethyl esters, and that n be 2 or 3. The benzocycloalkanethiophenemethyl esters wherein n is 3 and R is selected from 3-(2,2-dichloroethenyl)-2,2-dimethylcyclopropyl or 3-(2-chloro-3,3,3-trifluoro-1-propenyl)-2,2-dimethylcyclopropyl, e.g., the cis or 1R,cis isomers, are especially useful.

Also within the contemplation of this invention are insecticidal and acaricidal compositions comprising an insecticidally or acaricidally effective amount of active ester, e.g., benzocycloalkanethiophenemethyl ester, of this invention in admixture with an agriculturally acceptable carrier and a method of controlling insects or acarids which comprises applying to the locus where control is desired an insecticidally or acaricidally effective amount of active ester, e.g., benzocycloalkanethiophenemethyl ester, of this invention.

When the locus is soil, e.g. soil in which agricultural crops are planted, it may be advantageous to incorporate the active esters of this invention into the soil. This is especially effective in controlling certain pests, such as southern corn rootworm.

The active esters, e.g., benzocycloalkanethiophenemethyl esters, of this invention are prepared by reaction between a carbonyl halide, e.g., a chloride, RCOCl, wherein R is a pyrethroid acid residue; an acid, RCOOH; an ester, RCOOR', wherein R' is conveniently a $C_1$-$C_6$ alkyl group; an anhydride, RCOOR", wherein R" is $C_1$-$C_6$ alkylcarbonyl, or $C_1$-$C_6$ alkyl or aryl sulfonyl; or a nitrile, RCN, and an appropriate benzenecycloalkylheteroaromaticmethanol. Alternatively, they are prepared by reacting a salt, RCOOM, where M is an alkali or alkaline earth metal, e.g., Li, K, Na, Ca, or Mg, a transition metal, e.g., Ag, or ammonium or alkylsubstituted ammonium, with a benzenecycloalkylheteroaromaticmethyl compound wherein the benzylic carbon atom carries a leaving group which is readily displaced by carboxylate anions. Suitable leaving groups are known in the art and include, for example, halogen, especially bromine and chlorine; carboxylate, especially acetate; sulfonate, e.g.,

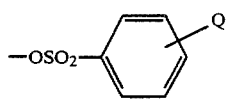

where Q is halogen, especially bromine, $C_1$–$C_6$ alkyl, e.g., p-toluene-sulfonate, nitro, or hydrogen, and —O—$SO_2C_RH_SF_T$ where R is 1–4, e.g., methanesulfonate, and S and T are independently 0–9; and —$NR_3X$, where R may be $C_1$–$C_6$ alkyl, and X may be halogen, sulfonate, or other readily available anion.

3-(2,2-Dichloroethenyl)- and 3-(2,2-dibromoethenyl)-2,2-dimethylcyclopropanecarboxylic acid and corresponding carbonyl chlorides are obtained by methods disclosed in U.S. Pat. No. 4,024,163. Carbonyl chlorides or corresponding salts wherein R is 2,2,3,3-tetramethylcyclopropyl, 2,2-dichloro-3,3-dimethylcyclopropyl, 3-cyclopentylidenemethyl-2,2-dimethylcyclopropyl, and 4-chloro-α-(1-methylethyl)phenylmethyl, are disclosed in *Agr. Biol. Chem.*, 31, 1143 (1967), *Agr. Biol. Chem.*, 38, 1511 (1974), U.S. Pat. No. 3,679,667, and *Agr. Biol. Chem.*, 39, 267 (1975), respectively. The 3-(2-methyl-1-propenyl)-2,2-dimethylcyclopropyl, 3-(1,2-dibromo-2,2-dichloroethyl)-2,2-dimethylcyclopropyl, and the set of 3-(2-chloro-3,3,3-trifluoro-1-propenyl)-2,2-dimethylcyclopropyl, 3-(3-chloro-2,3,3-trifluoro-1-propenyl)-2,2-dimethylcyclopropyl, and 3-(2,3-dichloro-3,3-difluoro-1-propenyl)-2,2-dimethylcyclopropyl acid residues are described in *Agr. Biol. Chem.*, 28, 27 (1961), and U.S. Pat. No. 4,179,575, respectively. The 4-difluoromethoxy-α-(1-methylethyl)phenylmethyl acid residue is disclosed in *Agr. Biol. Chem.*, 38, 881 (1974), while *Pestic. Sci.*, 7, 499 (1976) describes 3-(1,3-butadienyl)-2,2-dimethylcyclopropyl. U.S. Pat. No. 3,922,269, *Pestic. Sci.*, 11, 224 (1980), and U.S. Pat. No. 3,842,177 disclose 2,2-dimethyl-3-(oximinomethyl)cyclopropyl, 2-(2-chloro-α,α,α-trifluoro-p-toluidino)-3-methylbutyl, and 3-(2,3,4,5-tetrahydro-2-oxothien-3-ylidenemethyl)-2,2-dimethylcyclopropyl, respectively. *Nature*, 272, 734 (1978) describes 2,2-dichloro-1-(4-ethoxyphenyl)cyclopropyl. The spiro[2,2-dimethylcyclopropane-1,1′-[1H]indene]-3-yl acid residue appears in *Adv. Pestic. Sci., Plenary Lect. Symp. Paper Int. Congr. Pestic. Chem.*, 4th 1978, 2, p. 190. The remaining spiro acid residues are disclosed in "Synthetic Pyrethroids," ACS Symposium Series No. 42, Washington, D.C., 1977, page 37, while the 3-phenyl and substituted phenyl-2,2-dimethylcyclopropyl acid residues have been described by Farkas and Novak, *Coll. Czech. Chem. Comm.*, 25, 1815 (1960). The 4-halo-α-(1-cyclopropyl)phenylmethyl acid residues appear in *Abstracts, Fourth International Congress of Pesticide Chemistry*, Zurich, 1978. The 3-(1,2,2,2-tetrabromoethyl)-2,2-dimethylcyclopropyl acid residue is described in U.S. Pat. No. 4,231,932. These disclosures are also incorporated herein by reference.

The pure cis or trans benzocycloalkaneheteroaromaticmethyl esters are prepared either by reacting pure cis or pure trans acid derivatives with appropriate benzocycloalkaneheteroaromaticmethyl compounds or by separating cis,trans mixtures using chromatographic techniques.

Benzenecycloalkaneheteroaromaticmethyl, e.g., benzocycloalkanethiophenemethyl, compounds, which are intermediate in the preparation of many of the insecticidal esters, are novel compositions of matter and are also within the scope of this invention. These intermediates are described by Formula II

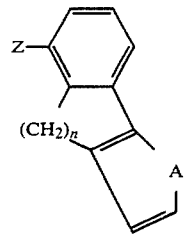

wherein Z is Y—$CH_2$— or $R_1$, A is —S—, —O—, or —N=CH—, preferably —S—, n is 1–4, especially 2 or 3, Y is hydroxyl or a leaving group readily displaced by carboxylate anions, as described above, and $R_1$ is chloro or bromo (preferably chloro), cyano, or hydroxycarbonyl.

Intermediates within the scope of this invention include, for example, 4,5-dihydronaphtho[1,2-b]thiophen-6-methanol, 4,5-dihydronaphtho[1,2-b]thiophen-6-methyl 4-methylphenylsulfonate, 4,5-dihydronaphtho[1,2-b]thiophen-6-methyl methanesulfonate, 4,5-dihydronaphtho[1,2-b]thiophen-6-methyl trifluoromethanesulfonate, 5,6-dihydro-4H-benzo[6,7]cyclohepta[1,2-b]-thiophen-7-methanol, 5,6-dihydro-4H-benzo[6,7]cyclohepta[1,2-b]-thiophen-7-methyl 4-methylphenylsulfonate, 5,6-dihydro-4H-benzo[6,7]cyclohepta[1,2-b]-thiophen-7-methyl methanesulfonate, 5,6-dihydro-4H-benzo[6,7]cyclohepta[1,2-b]thiophen-7-methyl trifluoromethanesulfonate and 5,6-dihydro-4H-benzo[6,7]cyclohepta[1,2-b]thiophen-7-methyl chloride when Z is Y—$CH_2$—. Intermediates within the scope of this invention include the following when Z is $R_1$: 6-chloro-4,5-dihydronaphtho[1,2-b]-thiophene, 6-cyano-4,5-dihydronaphtho[1,2-b]thiophene, 4,5-dihydronaphtho[1,2-b]thiophen-6-carboxylic acid, 7-chloro-5,6-dihydro-4H-benzo[6,7]cyclohepta[1,2-b]thiophene, 7-cyano-5,6-dihydro-4H-benzo[6,7]cyclohepta[1,2-b]thiophene, and 5,6-dihydro-4H-benzo[6,7]cyclohepta[1,2-b]thiophen-7-carboxylic acid. A benzocycloalkanethiophenemethyl alcohol can be converted into the corresponding methyl bromide by treating a solution of the alcohol in ether with phosphorous tribromide or phosphorous pentabromide. Similarly, a benzocycloalkanethiophenemethyl bromide can be converted into the corresponding alcohol by first treating the bromide with sodium acetate in acetic acid, and then treating the thus produced benzocycloalkanethiophenemethyl acetate with sodium hydroxide in methanol. In general, a chloromethyl compound is prepared by treating the corresponding methanol with thionyl chloride. The corresponding methyl methanesulfonate or methyl p-toluenesulfonate is prepared by treating the methanol with methanesulfonyl chloride or p-toluenesulfonyl chloride, respectively. These techniques are available in the prior art, as are methods for preparing the other intermediates of Formula II.

Preparation of specific compounds within the scope of this invention is illustrated below. Unless otherwise indicated, all temperatures are in degrees Celsius and pressures are in millimeters of mercury. Proton chemical shifts, taken from nmr spectra in $CDCl_3$, are reported in ppm with respect to tetramethylsilane.

EXAMPLE A

4,5-Dihydronaphtho[1,2-b]thiophen-6-methanol

Reaction of alpha-butyrolactone with chlorobenzene in the presence of aluminum chloride, as described in U.S. Pat. No. 3,657,400, produced 5-chloro-3,4-dihydro-1(2H)-naphthalenone. The latter was formylated with a combination of phosphorous oxychloride and dimethylformamide, yielding 1,5-dichloro-3,4-dihydronaphthalen-2-carboxaldehyde; mp 83.5°–84°, which was then reacted with ethyl thioglycolate and triethylamine in pyridine, as described in J.C.S. Perkin I, 2956 (1973), to produce ethyl 6-chloro-4,5-dihydronaphtho[1,2-b]thiophen-1-carboxylate; mp 81°–82°.

The ester was hydrolyzed with potassium hydroxide in ethanol, producing 6-chloro-4,5-dihydronaphtho[1,2-b]thiophen-1-carboxylic acid; mp 301° dec., which was decarboxylated using copper powder in quinoline by the procedure described in Org. Synth., Coll. Vol. 4, 628 (1963) to give 6-chloro-4,5-dihydronaphtho[1,2-b]thiophene as a light brown oil. Treatment of the 6-chloro compound with copper (I) cyanide in pyridine, as described in J. Am. Chem. Soc., 83, 943 (1961), produced 6-cyano-4,5-dihydronaphtho[1,2-b]thiophene; mp 74.5°–75° following purification.

To a stirred solution of 6-cyano-4,5-dihydronaphtho[1,2-b]-thiophene (4.1 g, 0.019 mole) in 75 ml of ethylene glycol, under a nitrogen atmosphere, was added potassium hydroxide [12.5 g, 0.19 mole). The reaction mixture was heated at 156°±5° for 18 hours. The cooled reaction mixture was diluted with 200 ml of cold water. The mixture was extracted with two 50 ml portions of diethyl ether. The aqueous layer was acidified with concentrated hydrochloric acid. The mixture was cooled and extracted with three 200 ml portions of diethyl ether. The extracts were combined, dried with magnesium sulfate, and filtered. The filtrate was concentrated under reduced pressure to give 4.4 grams of 4,5-dihydronaphtho[1,2-b]thiophen-6-carboxylic acid; mp 182°–184°.

Analysis: Calc'd for $C_{13}H_{10}O_2S$: C 67.81; H 4.37. Found: C 64.17; H 4.47.

To a stirred solution of 4,5-dihydronaphtho[1,2-b]thiophen-6-carboxylic acid (3.4 g, 0.015 mole) in 50 ml of tetrahydrofuran under an argon atmosphere was added dropwise borane-tetrahydrofuran complex (2.5 g, 0.030 mole). Upon complete addition, the reaction mixture was stirred at room temperature for 18.5 hours. The reaction mixture was then taken up in water and concentrated under reduced pressure to a residue. The residue was washed into a separatory funnel with aqueous 2N sodium hydroxide and methylene chloride. The aqueous layer was extracted with two 100 ml portions of methylene chloride. The combined extracts were dried with magnesium sulfate and filtered. The filtrate was concentrated under reduced pressure to give 4,5-dihydronaphtho[1,2-b]thiophen-6-methanol; 2.8 g, mp 99°–100°.

Analysis: Calc'd for $C_{13}H_{12}OS$: C 72.19; H 5.59. Found: C 71.64; H 5.34.

nmr: 1.85(bs,1H); 2.80–3.00(m,4H); 6.85–7.57(m,5H).

4,5-Dihydronaphtho[1,2-b]thiophen-6-methyl 4-methylphenylsulfonate and 4,5-dihydronaphtho[1,2-b]thiophen-6-methyl methanesulfonate are prepared by the method of Szeja, cited and specifically illustrated below.

EXAMPLE B

5,6-Dihydro-4H-benzo[6,7]cyclohepta-[1,2-b]thiophen-7-methanol

3-Chloro-2-methylaniline was treated with t-butylnitrite in excess thiophene as described in J. Chem. Soc., 4257 (1963) to produce 2-(3-chloro-2-methylphenyl)thiophene as an oil. Reaction of the oil with N-bromosuccinimide as described in J. Am. Chem. Soc., 89, 2348 (1967) yielded 2-(2-bromomethyl-3-chlorophenyl)thiophene as an oil, which was reacted without further purification, as described in J. Chem. Soc., 2708 (1955), with diethyl malonate in the presence of tetrabutyl ammonium bromide and potassium hydroxide in dry tetrahydrofuran, producing ethyl [2-carboethoxy-3-[2-chloro-6-(thien-2-yl)phenyl]]propionate. Hydrolysis of the latter with hydrochloric acid in glacial acetic acid provided 3-[2-chloro-6-(thien-2-yl)phenyl]propionic acid; mp 83°–86°.

The aforesaid acid was converted to 3-[2-chloro-6-(thien-2-yl)phenyl]propionyl chloride using oxalyl chloride in toluene as described in J. Am. Chem. Soc., 42, 699 (1920). The acyl chloride was cyclized with anhydrous aluminum chloride in carbon disulfide by an inverse Friedel-Crafts procedure described in J. Am. Chem. Soc., 71, 1092 (1949), producing 7-chloro-4,5-dihydro-4H-benzo-[6,7]cyclohepta[1,2-b]thiophen-4-one.

The aforesaid ketone was subsequently reduced to 7-chloro-5,6-dihydro-4H-benzo[6,7]cyclohepta[1,2-b]thiophene using hydrazine hydrate and potassium hydroxide in ethylene glycol by the method described in J. Am. Chem. Soc., 78, 1012 (1956). The 7-chloro compound was converted to 7-cyano-5,6-dihydro-4H-benzo[6,7]cyclohepta[1,2-b]thiophene with copper(I) cyanide in hot pyridine as in Example A.

In the manner of Example A, 5,6-dihydro-4H-benzo[6,7]-cyclohepta[1,2-b]thiophen-7-carboxylic acid; mp 160.5°–160.8°, was prepared using 7-cyano-5,6-dihydro-4H-benzo-[6,7]cyclohepta-[1,2-b]thiophene (7.1 g, 0.031 mole) and 85% potassium hydroxide (20.4 g, 0.310 mole) in 125 ml of ethylene glycol.

In the manner of Example A, 5,6-dihydro-4H-benzo[6,7]cyclohepta[1,2-b]thiophen-7-methanol, an oil, was prepared using 5,6-dihydro-4H-benzo[6,7]cyclohepta[1,2-b]thiophen-7-carboxylic acid (6.2 g, 0.025 mole) and 38 ml (0.038 mole) of borane-tetrahydrofuran complex in 100 ml of tetrahydrofuran. The yield of 5,6-dihydro-4H-benzo[6,7]cyclohepta[1,2-b]thiophen-7-methanol was 5.8 grams.

Analysis: Calc'd for $C_{14}H_{14}OS$: C 73.01; H 6.13. Found: C 73.06; H 6.40.

nmr: 1.93–2.77(m,7H); 4.70(s,2H); 6.87–7.50(m,5H).

EXAMPLE C

5,6-Dihydro-4H-benzo[6,7]cyclohepta[1,2-b]thiophen-7-methyl Chloride

A stirred solution of 5,6-dihydro-4H-benzo[6,7]cyclohepta[1,2-b]thiophen-7-methanol (5.0 g, 0.023 mole), methanesulfonyl chloride (5.0 g, 0.004 mole), and pyridine (3.4 g, 0.044 mole) in 50 ml of carbon tetrachloride was heated under reflux for 16 hours. The reaction mixture was then placed in a separatory funnel and washed with 50 ml of aqueous 2N hydrochloric acid, followed with 50 ml of aqueous 2N sodium hydroxide. The organic layer was dried with magnesium sulfate and filtered. The filtrate was concentrated under reduced pressure to an oily residue. The oil was subjected to column chromatography on silica gel, elution with 3:2 toluene:heptane. The appropriate fractions were combined and concentrated under reduced pressure to give 3.0 grams of 5,6-dihydro-4H-benzo[6,7]cyclohepta[1,2-b]thiophen-7-methyl chloride, a solid.

Analysis: nmr: 2.07–2.90(m,6H); 4.70(s,2H); 6.90–7.53(m,5H).

5,6-Dihydro-4H-benzo[6,7]cyclohepta[1,2-b]thiophen-7-methyl 4-methylsulfonate is prepared by the method of Szeja, *Synthesis*, 822 (1979). A solution of 4-methylphenylsulfonyl chloride (21 g, 0.11 mole) in 50 ml of toluene is added dropwise to a stirred mixture of 5,6-dihydro-4H-benzo[6,7]cyclohepta[1,2-b]thiophene-7p-methanol (23 g, 0.1 mole) and phenylmethyltriethylammonium bromide (0.91 g, 0.004 mole) in 30% aqueous sodium hydroxide solution maintained at 20°–25°. The reaction mixture is stirred for 5–8 hours. The organic layer is separated, washed with water until neutral, then dried with anhydrous sodium sulfate. The mixture is filtered and the filtrate concentrated under reduced pressure to give 5,6-dihydro-4H-benzo[6,7]cyclohepta[1,2-b]thiophen-7-methyl 4-methylphenylsulfonate.

5,6-Dihydro-4H-benzo[6,7]cyclohepta[1,2-b]thiophen-7-methyl methanesulfonate is also prepared by the method of Szeja cited above. A solution of 5,6-dihydro-4H-benzo[6,7]cyclohepta[1,2-b]thiophen-7-methanol (23 g, 0.1 mole) and phenylmethyltriethylammonium chloride (0.23 g, 0.001 mole) in 100 ml of dichloromethane is stirred with 50 ml of 30% aqueous sodium hydroxide solution. The mixture is cooled to −5°, and a solution of methanesulfonyl chloride in 50 ml of dichloromethane (17.1 g, 0.15 mole) is added dropwise at a rate to maintain the temperature of the reaction mixture below 0°. The reaction mixture is stirred for an additional 10 minutes after complete addition. The organic layer is separated, washed with water until neutral, then dried with anhydrous sodium sulfate. The mixture is filtered and the filtrate concentrated under reduced pressure to give 5,6-dihydro-4H-benzo[6,7]cyclohepta[1,2-b]thiophen-7-methyl methanesulfonate.

EXAMPLE 19

5,6-Dihydro-4H-benzo[6,7]cyclohepta[1,2-b]thiophen-7-methyl cis-3-(2-chloro-3,3,3-trifluoro-1-propenyl)-2,2-dimethylcyclopropanecarboxylate A stirred solution of 5,6-dihydro-4H-benzo[6,7]cyclohepta[1,2-b]thiophen-7-methanol (1.00 g, 0.004 mole) and pyridine (0.5 g, 0.004 mole) in 30 ml of toluene was warmed to 45°, and cis-3-(2-chloro-3,3,3-trifluoro-1-propenyl)-2,2-dimethylcyclopropanecarbonyl chloride (1.1 g, 0.004 mole) in 2 ml of toluene was added dropwise. Upon complete addition, the reaction mixture was allowed to cool to room temperature, where it was stirred for 16 hours. The reaction mixture was then poured into a separatory funnel. The reaction vessel was rinsed with three 100 ml portions of heptane. The rinses were added to the separatory funnel, and the combination was washed with 100 ml of aqueous 2N ammonium chloride, 75 ml of an aqueous saturated sodium chloride solution, 125 ml of aqueous 2N sodium hydroxide, and finally 10 ml of the aqueous solution saturated with sodium chloride. The mixture was filtered and concentrated under reduced pressure to a residual oil. The oil was subjected to column chromatography on silica gel, elution with toluene. The appropriate fractions were combined and concentrated under reduced pressure to give 4,5-dihydro-4H-benzo[6,7]cyclohepta[1,2-b]thiophen-7-methyl cis-3-(2-chloro-3,3,3-trifluoro-1-propenyl)-2,2-dimethylcyclopropanecarboxylate, 1.4 g as an oil.

Analysis: Calc'd for $C_{22}H_{22}ClF_3O_2S$: C 59.66; H 5.01. Found: C 60.25; H 4.93.

nmr: 1.30(s,6H); 1.97–2.83(m,8H); 5.27(s,2H); 6.92–7.53(m,6H).

EXAMPLE 26

5,6-Dihydro-4H-benzo[6,7]cyclohepta[1,2-b]thiophen-7-methyl 2-(2-chloro-4-trifluoromethylanilino)-3-methylbutyrate To a stirred solution of 85% potassium hydroxide (1.0 g, 0.004 mole) in 1 ml of water was added 2-(2-chloro-4-trifluoromethylanilino)-3-methylbutyric acid (1.1 g, 0.004 mole). When all of the acid was dissolved, the reaction mixture was slurried with 60 ml of heptane and all of the water removed by distillation. The reaction mixture was cooled to room temperature, and 0.1 gram of 1,4-diazabicyclo[2.2.2]octane and 5,6-dihydro-4H-benzo[6,7]cyclohepta[1,2-b]thiophen-7-methyl chloride (1.0 g, 0.004 mole) in 30 ml of acetonitrile were added. The reaction mixture was heated under reflux for 18 hours and then transferred to a separatory funnel. The reaction vessel was rinsed with toluene, aqueous 2N sodium hydroxide and water. The rinses were added to the separatory funnel. The aqueous layer was separated and extracted with two 100 ml portions of toluene. The organic layers were combined and washed with 200 ml of aqueous 2N hydrochloric acid, then dried with magnesium sulfate. The mixture was filtered and the filtrate concentrated under reduced pressure to an oily residue. The oil was subjected to column chromatography on silica gel, elution with toluene. The appropriate fractions were combined and concentrated under reduced pressure to give 5,6-dihydro-4H-benzo[6,7]cyclohepta[1,2-b]thiophen-7-methyl 2-(2-chloro-4-trifluoromethylanilino)-3-methylbutyrate; 0.97 g as an oil.

Analysis: Calc'd for $C_{26}H_{25}ClF_3NO_2S$: C 61.44; H 4.95. Found: C 61.90; H 5.05.

nmr: 0.95–1.10(dd,6H); 1.97–2.80(m,7H); 3.78–4.10(dd,1H); 5.07–5.20(bd,1H); 5.30(s,2H); 6.53–7.55(m,8H).

Other benzocycloalkanethiophenemethyl esters of this invention were similarly prepared and are listed below, together with analyses; all were oils.

EXAMPLE 1

4,5-Dihydronaphtho[1,2-b]thiophen-6-methyl cis-3-(2,2-dichloroethenyl)-2,2-dimethylcyclopropanecarboxylate Analysis: Calc'd for $C_{21}H_{20}Cl_2O_2S$: C 61.92; H 4.94. Found: C 62.26; H 4.77.

nmr: 1.17–1.27(dd,6H); 1.43–2.23(m,2H); 2.83–3.00(m,4H); 5.20(s,2H); 5.57–6.37(dd,1H); 6.87–7.50(m,5H)

EXAMPLE 2

4,5-Dihydronaphtho[1,2-b]thiophen-6-methyl trans-3-(2,2-dichloroethenyl)-2,2-dimethylcyclopropanecarboxylate Analysis: Calc'd for $C_{21}H_{20}Cl_2O_2S$: C 61.92; H 4.94. Found: C 61.50; H 4.66.

nmr: 1.14(s,3H); 1.30(s,3H); 1.60–2.30(m,2H); 2.83–3.00(m,4H); 5.23(s,2H); 5.57–5.70(d,1H); 6.87–7.50(m,5H).

EXAMPLE 3

4,5-Dihydronaphtho[1,2-b]thiophen-6-methyl 1R-cis-3-(2,2-dichloroethenyl)-2,2-dimethylcyclopropanecarboxylate Analysis: Calc'd for $C_{21}H_{20}Cl_2O_2S$: C 61.92; H 4.94. Found: C 62.26; H 4.65.

nmr: 1.23–1.27(d,6H); 1.78–2.05(m,2H); 2.83–3.00(m,4H); 5.20(s,2H); 6.27–6.38(dd,1H); 6.83–7.63(m,5H).

EXAMPLE 4

4,5-Dihydronaphtho[1,2-b]thiophen-6-methyl cis-3-(2,2-dibromoethenyl)-2,2-dimethylcyclopropanecarboxylate Analysis: Calc'd for $C_{21}H_{20}Br_2O_2S$: C 50.83; H 4.06. Found: C 50.79; H 4.22.

nmr: 1.23–1.27(d,6H); 1.77–2.00(m,2H); 2.83–3.00(m,4H); 5.20(s,2H); 6.73–7.50(m,6H).

EXAMPLE 5

4,5-Dihydronaphtho[1,2-b]thiophen-6-methyl 1R-cis-3-(1,2-dibromo-2-2-dichloroethyl)-2,2-dimethylcyclopropanecarboxylate Analysis: Calc'd for $C_{21}H_{19}Br_2Cl_2O_2S$: C 44.55; H 3.38. Found: C 42.81; H 3.70.

nmr: 1.23–1.27(d,3H); 1.40–1.43(d,3H); 1.82–2.07(m,2H); 2.82–3.00(m,4H); 5.07–5.57(m,3H); 6.83–7.50(m,5H).

EXAMPLE 6

4,5-Dihydronaphtho[1,2-b]thiophen-6-methyl 1R-cis-3-(1,2,2,2-tetrabromoethyl)-2,2-dimethylcyclopropanecarboxylate Analysis: Calc'd for $C_{21}H_{19}Br_4O_2S$: C 38.50; H 2.92. Found: C 39.51; H 3.33.

nmr: 1.27(bs,3H); 1.40–1.47(d,3H); 1.82–2.12(m,2H); 2.82–3.00(m,4H); 5.00–5.63(m,1H); 5.20–5.27(d,2H); 6.87–7.50(m,5H).

EXAMPLE 7

4,5-Dihydronaphtho[1,2-b]thiophen-6-methyl cis-3-(2-chloro-3,3,3-trifluoro-1-propenyl)-2,2-dimethylcyclopropanecarboxylate Analysis: Calc'd for $C_{22}H_{20}ClF_3O_2S$: C 59.93; H 4.57. Found: C 60.86; H 4.47.

nmr: 1.30(bs,6H); 1.97–2.30(m,2H); 2.83–3.00(m,4H); 5.27(s,2H); 6.87–7.63(m,6H).

EXAMPLE 8

4,5-Dihydronaphtho[1,2-b]thiophen-6-methyl cis-3-(3-chloro-2,3,3-trifluoro-1-propenyl-2,2-dimethylcyclopropanecarboxylate Analysis: Calc'd for $C_{22}H_{20}ClF_3O_2S$: C 59.93; H 4.57. Found: C 60.50; H 4.56.

nmr: 1.27(bs,6H); 1.83–2.30(m,4H); 2.83–3.00(m,4H); 5.20(s,2H); 5.70–6.43(bq,1H); 6.87–7.50(m,5H).

EXAMPLE 9

4,5-Dihydronaphtho[1,2-b]thiophen-6-methyl 3,3-dichloro-2,2-dimethylcyclopropanecarboxylate Analysis: Calc'd for $C_{19}H_{18}Cl_2O_2S$: C 59.85; H 4.75. Found: C 59.58; H 5.06.

nmr: 1.47(s,3H); 1.48(s,3H); 2.17(s,1H); 2.83–3.02(m,4H); 5.27(s,2H); 6.87–7.50(m,5H).

EXAMPLE 10

4,5-Dihydronaphtho[1,2-b]thiophen-6-methyl 2,2,3,3-tetramethylcyclopropanecarboxylate Analysis: Calc'd for $C_{21}H_{24}O_2S$: C 74.09; H 7.10. Found: C 73.25; H 7.47.

nmr: 1.17(s,6H); 1.27(s,6H); 1.20(s,1H); 2.80–3.00(m,4H); 5.17(s,2H); 6.83–7.47(m,5H).

EXAMPLE 11

4,5-Dihydronaphtho[1,2-b]thiophen-6-methyl 1R-trans-3-(cyclopentylidinemethyl)-2,2-dimethylcyclopropanecarboxylate Analysis: Calc'd for $C_{24}H_{28}O_2S$: C 75.75; H 7.41. Found: C 76.41; H 7.15.

nmr: 1.15–1.28(d,6H); 1.42–2.45(m,8H); 2.83–3.00(m,4H); 4.93–5.43(m,1H); 5.20(m,5H).

EXAMPLE 12

4,5-Dihydronaphtho[1,2-b]thiophen-6-methyl 1-(4-ethoxyphenyl)-2,2-dichlorocyclopropanecarboxylate Analysis: Calc'd for $C_{25}H_{22}Cl_2O_3S$: C 63.43; H 4.68. Found: C 63.09; H 4.69.

nmr: 1.27–1.50(t,3H); 1.93–2.67(q,2H); 2.77(s,4H); 3.82–4.17(q,2H); 5.23(s,2H).

EXAMPLE 13

4,5-Dihydronaphtho[1,2-b]thiophen-6-methyl 4-chloro-α-(1-methylethyl)benzeneacetate Analysis: Calc'd for $C_{24}H_{23}ClO_2S$: C 70.15; H 5.64. Found: C 71.05; H 5.45.

nmr: 0.65–0.73(d,3H); 0.93–1.07(d,3H); 2.72(s,4H); 3.10–3.27(d,1H); 5.17(s,2H); 6.90–7.47(m,9H).

EXAMPLE 14

5,6-Dihydro-4H-benzo[6,7]cyclohepta[1,2-b]thiophen-7-methyl cis-3-(2,2-dichloroethenyl)-2,2-dimethylcyclopropanecarboxylate Analysis: Calc'd for $C_{22}H_{22}Cl_2O_2S$: C 62.71; H 5.26. Found: C 62.46; H 5.19.

nmr: 1.23–1.27(d,6H); 1.80–2.83(m,8H); 5.23(s,2H); 6.20–6.37(dd,1H); 6.90–7.50(m,5H).

EXAMPLE 15

5,6-Dihydro-4H-benzo[6,7]cyclohepta[1,2-b]thiophen-7-methyl trans-3-(2,2-dichloroethenyl)-2,2-dimethylcyclopropanecarboxylate Analysis: Calc'd for $C_{22}H_{22}Cl_2O_2S$: C 62.71; H 5.26. Found: C 62.38; H 5.04.

nmr: 1.20–1.30(d,6H); 1.63–2.83(m,8H); 5.27(s,2H); 5.60–5.70(d,2H); 6.90–7.53(m,5H).

EXAMPLE 16

5,6-Dihydro-4H-benzo[6,7]cyclohepta[1,2-b]thiophen-7-methyl
1R-cis-3-(2,2-dichloroethenyl)-2,2-dimethylcyclopropanecarboxylate Analysis: Calc'd for $C_{22}H_{22}Cl_2O_2S$: C 62.71; H 5.26. Found: C 62.57; H 5.29.

nmr: 1.23–1.27(d,6H); 1.80–2.83(m,8H); 5.23(s,2H); 6.23–6.38(dd,1H); 6.90–7.53(m,5H).

EXAMPLE 17

5,6-Dihydro-4H-benzo[6,7]cyclohepta[1,2-b]thiophen-7-methyl
1R-cis-3-(1,2-dibromo-2,2-dichloroethyl)-2,2-dimethylcyclopropanecarboxylate Analysis: Calc'd for $C_{22}H_{22}Cl_2Br_2O_2S$: C 45.47; H 3.81. Found: C 44.69; H 3.58.

nmr: 1.20–1.23(d,3H); 1.37–1.43(d,3H); 1.70–2.83(m,8H); 5.08–5.60(m,1H); 5.25–5.30(d,2H); 6.92–7.57(m,5H).

EXAMPLE 18

5,6-Dihydro-4H-benzo[6,7]cyclohepta[1,2-b]thiophen-7-methyl
1R-cis-3-(1,2,2,2-tetrabromoethyl)-2,2-dimethylcyclopropanecarboxylate Analysis: Calc'd for $C_{22}H_{22}Br_4O_2S$: C 39.43; H 3.31. Found: C 40.69; H 3.43.

nmr: 1.20–1.25(d,3H); 1.40–1.53(d,3H); 1.83–2.87(m,8H); 5.08–5.68(m,1H); 5.27–5.30(d,2H); 6.90–7.53(m,5H).

EXAMPLE 20

5,6-Dihydro-4H-benzo[6,7]cyclohepta[1,2-b]thiophen-7-methyl
cis-3-(3-chloro-2,3,3-trifluoro-1-propenyl)-2,2-dimethylcyclopropanecarboxylate Analysis: Calc'd for $C_{23}H_{22}ClF_3O_2S$: C 60.73; H 4.87. Found: C 60.95; H 4.84.

nmr: 1.27(s,6H); 1.85–2.80(m,8H); 5.23(s,2H); 5.73–6.43(dd,1H); 6.88–7.55(m,5H).

EXAMPLE 21

5,6-Dihydro-4H-benzo[6,7]cyclohepta[1,2-b]thiophen-7-methyl
3,3-dichloro-2,2-dimethylcyclopropanecarboxylate Analysis: Calc'd for $C_{20}H_{20}Cl_2O_2S$: C 60.76; H 5.09. Found: C 60.49; H 4.96.

nmr: 1.47(s,8H); 1.50(s,3H); 2.03–2.83(m,7H); 5.30(s,2H); 6.90–7.53(m,5H).

EXAMPLE 22

5,6-Dihydro-4H-benzo[6,7]cyclohepta[1,2-b]thiophen-7-methyl 2,2,3,3-tetramethylcyclopropanecarboxylate Analysis: Calc'd for $C_{22}H_{26}O_2S$: C 74.52; H 7.39. Found: C 73.95; H 7.50.

nmr: 1.20(s,6H); 1.27(s,6H); 2.00–2.87(m,7H); 5.27(s,2H); 6.90–7.42(m,5H).

EXAMPLE 23

5,6-Dihydro-4H-benzo[6,7]cyclohepta[1,2-b]thiophen-7-methyl
1R-trans-3-(cyclopentylidinemethyl)-2,2-dimethylcyclopropanecarboxylate Analysis: Calc'd for $C_{26}H_{29}O_2S$: C 77.00; H, 7.20; Found: C 76.55; H 7.17.

nmr: 1.15(s,3H); 1.28(s,3H); 1.43–2.03(m,15H); 4.83–5.30(m,1H); 5.28(s,2H); 6.93–7.37(m,5H).

EXAMPLE 24

5,6-Dihydro-4H-benzo[6,7]cyclohepta[1,2-b]thiophen-7-methyl
1-(4-ethoxyphenyl)-2,2-dichlorocyclopropanecarboxylate Analysis: Calc'd for $C_{26}H_{24}Cl_2O_3S$: C 64.07; H 4.96. Found: C 63.24; H 5.04.

nmr: 1.27–1.50(t,3H); 1.93–2.68(m,8H); 3.83–4.20(q,2H); 5.27(s,2H); 6.77–7.50(m,9H).

EXAMPLE 25

5,6-Dihydro-4H-benzo[6,7]cyclohepta[1,2-b]thiophen-7-methyl 4-chloro-α-(1-methylethyl)-benzeneacetate Analysis: Calc'd for $C_{25}H_{25}ClO_2S$: C 70.66; H 5.92. Found: C 71.35; H 6.04.

nmr: 0.63–0.75(d,3H); 0.97–1.07(d,3H); 1.87–2.63(m,7H); 3.10–3.28(d,1H); 5.22(s,2H); 6.87–7.50(m,9H).

In the normal use of the insecticidal and acaricidal esters of the present invention, the esters usually will not be employed free from admixture or dilution, but ordinarily will be used in a suitable formulated composition compatible with the method of application and comprising an insecticidally or acaricidally effective amount of benzocycloalkaneheteroaromaticmethyl ester. The esters of this invention, like most pesticidal agents, may be blended with the agriculturally acceptable surface-active agents and carriers normally employed for facilitating the dispersion of active ingredients, recognizing the accepted fact that the formulation and mode of application of an insecticide or acaricide may affect the activity of the material. The present esters may be applied, for example, as sprays, dusts, or granules to the area where pest control is desired, the type of application varying of course with the pest and the environment. Thus, the esters of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for the esters. The granule particles are relatively large, a diameter of about 400–2500 microns typically. The particles are either impregnated with the ester from solution or coated with the ester, adhesive sometimes being employed. Granules generally contain 0.05–10%, preferably 0.5–5%, active ingredient as the insecticidally effective amount.

Dusts are admixtures of the esters with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects and acarids contain 1 part of benzocycloalkanethiophenemethyl ester, such as 5,6-dihydro-4H-benzo[6,7]cyclohepta[1,2-b]thiophen-7-methyl cis-3-(2-chloro-3,3,3-trifluoro-1-propenyl)-2,2-dimethylcyclopropanecarboxylate, and 99 parts of talc.

The esters of the present invention may be made into liquid concentrates by dissolution or emulsification in suitable liquids and into solid concentrates by admixture with talc, clays, and other known solid carriers used in the pesticide art. The concentrates are compositions containing, as an insecticidally or acaricidally effective amount, about 5–50% benzocycloalkanethiophenemethyl ester, such as 5,6-dihydro-4H-benzo[6,7-]cyclohepta[1,2-b]thiophen-7-methyl cis-3-(2-chloro-3,3,3-trifluoropropenyl)-2,2-dimethylcyclopropanecarboxylate, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

Typical carriers for solid concentrates (also called wettable powders) include fuller's earth, clays, silicas, and other highly absorbent, readily wetted inorganic diluents. A solid concentrate formulation useful for controlling insects and acarids contains 1.5 parts each of sodium lignosulfonate and sodium laurylsulfate as wetting agents, 25 parts of 5,6-dihydro-4H-benzo[6,7]cyclohepta[1,2-b]thiophen-7-methyl cis-3-(2-chloro-3,3,3-trifluoropropenyl)-2,2-dimethylcyclopropanecarboxylate, and 72 parts of attapulgite clay.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active ester with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal and acaricidal composition.

Other useful formulations include simple solutions of the active ingredient in a solvent in which it is completely soluble at the desired concentration, such as acetone or other organic solvents.

An insecticidally or acaricidally effective amount of active benzocycloalkanethiophenemethyl ester in an insecticidal or acaricidal composition diluted for application is normally in the range of about 0.001% to about 8% by weight. Many variations of spraying and dusting compositions known in the art may be used by substituting the esters of this invention into compositions known or apparent to the art.

The insecticidal or acaricidal compositions of this invention may be formulated with other active ingredients, including other insecticides, nematicides, acaricides, fungicides, plant growth regulators, fertilizers, etc. In using the compositions to control insects and acarids, it is only necessary that an insecticidally or acaricidally effective amount of active benzocycloalkaneheteroaromaticmethyl ester be applied to the locus where control is desired. When the locus is soil, e.g., soil in which agricultural crops are planted, the active compound may be applied to and optionally incorporated into the soil. For most applications, an insecticidally or acaricidally effective amount will be about 10 to 2000 g per hectare, preferably 50 g to 1000 g per hectare.

The insecticidal and acaricidal activity of the benzocycloalkanethiophenemethyl esters, whose preparation is described above, were evaluated as follows:

The activity was evaluated in topical application to one or more of southern armyworm (*Spodoptera eridania*), Mexican bean beetle (*Epilachna varivestis*), cabbage looper (*Trichoplusia ni*), large milkweed bug (*Oncopeltus fasciatus*), tobacco budworm (*Heliothis virescens*), and southern corn rootworm (*Diabrotica undecimpunctata*). Two replicates of 10 test larvae per replicate were placed in 9 cm petri dishes, each lined with a piece of filter paper and a food source. On the second or third dorsal thoracic segment of each larva was placed a 1 microliter droplet containing the desired amount of the test compound in acetone. The toxic effect of the compound was determined 24 hours after application. An insect was considered dead if it could no longer right itself and move in an oriented pattern. The results of these tests appear in Table 1.

The compounds were also tested in foliar applications at various concentrations in aqueous solutions containing 10% acetone and 0.25% emulsifier. The plants (English fava bean for pea aphid and pinto bean for the remaining species) were placed on a revolving turntable in a hood, and the test solutions were applied with a sprayer. The test solutions were applied to the upper and lower surfaces of the plant leaves while the turntable revolved 10 times (5 for upper surface and 5 for lower surface). The total spray time was approximately one minute, and the leaves were covered to runoff. In every case the lowest rate was applied first and the highest rate last. The plants were then allowed to dry. The treated leaves were removed and placed in 240 ml or 480 ml wax treated containers. Ten individuals of the appropriate species were placed in each container and the container capped. Mortality was read 48 hours post-treatment unless otherwise noted. Two replicates of ten individuals were made at each rate. Foliar evaluation used southern armyworm (*Spodoptera eridania*), Mexican bean beetle (*Epilachna varivestis*), pea aphid (*Acyrthosiphon pisum*), cabbage looper (*Trichoplusia ni*) and twospotted spider mite (*Tetranychus urticae*). The results of the foliar tests appear in Table 2.

TABLE 1

Topical Evaluation

| Compound of Ex. | Insects[a] [LD$_{50}$ (ng/insect)] | | | | | |
|---|---|---|---|---|---|---|
| | MWB | SAW | SCR | MBB | CL | TBW |
| 1 | 2526 | 175 | 104 | | | |
| 2 | 2643 | 265 | | | | |
| 3 | 372 | 64 | 82 | | | |
| 4 | 2593 | 263 | 137 | | | |
| 5 | 2281 | 226 | | | | |
| 6 | 3255 | 1202 | | | | |
| 7 | 680 | 48 | 66 | | | |
| 8 | 875 | 182 | | | | |
| 9 | [b] | 4011 | | | | |
| 10 | 4262 | 597 | | | | |
| 11 | 1760 | 957 | | | | |
| 12 | [b] | [b] | | | | |
| 13 | [b] | [b] | | | | |
| 14 | 196 | 21 | [c] | 28 | 231 | 122 |
| 15 | 945 | 84 | 177 | | | |
| 16 | 42 | 15 | [c] | 13 | 126 | 71 |
| 17 | 1454 | 42 | 62 | | | |
| 18 | 930 | 67 | 85 | | | |
| 19 | 50 | 32 | 7 | 21 | 72 | 63 |
| 20 | 641 | 85 | 101 | | | |
| 21 | 1416 | 553 | | | | |
| 22 | 1792 | 93 | 250 | | | |
| 23 | 945 | 351 | 156 | | | |
| 24 | [b] | [b] | | | | |
| 25 | 2455 | [b] | | | | |

[a]MBB = Mexican bean beetle
MWB = milkweed bug
SAW = southern armyworm
SCR = southern corn rootworm
CL = cabbage looper
TBW = tobacco budworm
[b]zero kill at highest rate, 5000 ng/insect
[c]100% kill at 2500 ng/insect

TABLE 2

| Compound of Ex. | Rate (ppm) | Foliar Evaluation Insects[a] (% Kill) | | | | |
|---|---|---|---|---|---|---|
| | | PA | SAW | TSM | MBB | CL |
| 1 | 1250 | 100 | 100 | 60 | | 90 |
| | 64 | 65 | 55 | | | 45 |
| 2 | 1250 | 100 | 100 | 80 | | 95 |
| | 64 | 0 | 40 | 0 | | 25 |
| 3 | 1250 | 100 | 100 | 100 | | 100 |
| | 64 | 100 | 95 | 0 | | 75 |
| 4 | 1250 | 100 | 100 | 90 | | 85 |
| | 64 | 80 | 70 | 0 | | 40 |
| 5 | 1250 | 100 | 100 | 0 | | 100 |
| | 64 | 40 | 85 | | | 75 |
| 6 | 1250 | 85 | 100 | 0 | | 100 |
| | 64 | 45 | 30 | | | 30 |
| 7 | 1250 | 95 | 100 | 100 | | 100 |
| | 64 | 95 | 95 | 0 | | 100 |
| 8 | 1250 | 100 | 100 | 100 | | 95 |
| | 64 | 50 | 40 | 0 | | 100 |
| 9 | 1250 | 100 | 100 | 0 | | 100 |
| | 64 | 0 | 0 | | | 0 |
| 10 | 1250 | 100 | 100 | 100 | | 90 |
| | 64 | 0 | 75 | 0 | | 60 |
| 11 | 1250 | 100 | 100 | 0 | | 100 |
| | 64 | 20 | 0 | | | 0 |
| 12 | 1250 | 70 | 45 | 0 | | 100 |
| | 64 | 0 | 0 | | | 45 |
| 13 | 1250 | 35 | 90 | 30 | | 80 |
| | 64 | | 0 | | | 0 |
| 14 | 500 | 100 | 100 | 100 | | |
| | 64 | 100 | | 0 | 100 | 100 |
| | 16 | 80 | | | 55 | 100 |
| | 4 | 35 | | | 10 | 60 |
| 15 | 1250 | 80 | 100 | 60 | | 100 |
| | 64 | 85 | 80 | | | 95 |
| 16 | 500 | 100 | 100 | 100 | | |
| | 64 | 80 | | 26 | 100 | 100 |
| | 16 | 90 | | | 80 | 95 |
| | 4 | 50 | | | 10 | 55 |
| 17 | 1250 | 100 | 100 | 60 | | 100 |
| | 16 | 35 | 30 | | | 90 |
| 18 | 1250 | 100 | 100 | 50 | | 100 |
| | 16 | 65 | 15 | | 70 | |
| 19 | 500 | 100 | 100 | 100 | | |
| | 8 | 90 | 95 | 4 | 57.5 | 95 |
| | 2 | 67.5 | 15 | | 10 | 65 |
| | 1 | 35 | 10 | | 0 | |
| 20 | 1250 | 100 | 100 | 100 | | 100 |
| | 64 | 80 | 100 | 0 | | 100 |
| 21 | 1250 | 100 | 100 | 70 | | 90 |
| | 64 | 35 | 40 | 0 | | 35 |
| 22 | 1250 | 100 | 100 | 100 | | 100 |
| | 64 | 50 | 100 | 0 | | 70 |
| 23 | 1250 | 100 | 100 | 100 | | 100 |
| | 64 | 70 | 20 | 0 | | 30 |
| 24 | 1250 | 100 | 100 | 0 | | 100 |
| | 64 | 20 | 0 | | | 70 |
| 25 | 1250 | 100 | 100 | 70 | | 100 |
| | 64 | 45 | 5 | 0 | | 35 |
| 26 | 1250 | 100 | 0 | 0 | | 100 |
| | 8 | | | | | 50 |

[a]MBB = Mexican bean beetle
PA = pea aphid
SAW = southern armyworm
CL = cabbage looper
TSM = twospotted spider mite

What is claimed is:

1. Insecticidal benzocycloalkanethiophenemethyl esters of the formula

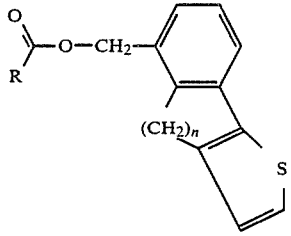

wherein n is 2 or 3 and R is selected from the group consisting of 3-(2,2-dihaloethenyl)-2,2-dimethylcyclopropyl; 3-(cyclopentylidenemethyl)-2,2-dimethylcyclopropyl; 3-(2-methyl-1-propenyl)-2,2-dimethylcyclopropyl; 3-(1,2-dibromo-2,2-dichloroethyl)-2,2-dimethylcyclopropyl; 3-(1,2,2,2-tetrabromoethyl)-2,2-dimethylcyclopropyl; 3-(2-chloro-3,3,3-trifluoro-1-propenyl)-2,2-dimethylcyclopropyl; 3-(3-chloro-2,3,3-trifluoro-1-propenyl)-2,2-dimethylcyclopropyl; 3-(2,3-dichloro-3,3-difluoro-1-propenyl)-2,2-dimethylcyclopropyl; 2,2,3,3-tetramethylcyclopropyl; 2,2-dichloro-3,3-dimethylcyclopropyl; 4-chloro-α-(1-methylethyl)phenylmethyl; 4-difluoromethoxy-α-(1-methylethyl)phenylmethyl; 3-(1,3-butadienyl)-2,2-dimethylcyclopropyl; 2,2-dimethyl-3-(oximinomethyl)cyclopropyl; 2-(2chloro-α,α,α-trifluoro-p-toluidino)-3-methylbutyl; 3-(2,3,4,5-tetrahydro-2-oxothien-3-ylidenemethyl)-2,2-dimethylcyclopropyl; 2,2-dichloro-1-(4-ethoxyphenyl)-cyclopropyl; 4-halo-α-(1-cyclopropyl)phenylmethyl; spiro[2,2-dimethylcyclopropane-1,1'-[1H]-indene-3-yl; spiro[3-(2,2-dichloroethenyl)cyclopropane-1,1'-cyclohexane]-2-yl; spiro[3-(2,2-dichloroethenyl)cyclopropane-1,1'-cyclobutane]-2-yl; 3-phenyl-2,2-dimethylcyclopropyl; 3-(4-halophenyl)-2,2-dimethylcyclopropyl; 3-(4-methoxyphenyl)-2,2-dimethylcyclopropyl; 3-(4-ethoxyphenyl)-2,2-dimethylcyclopropyl; and 3-(3,4-methylenedioxyphenyl)-2,2-dimethylcyclopropyl.

2. The esters of claim 1 wherein R is selected from 3-(2,2-dichloroethenyl)-2,2-dimethyl-2,2-dimethylcyclopropyl and 3-(2-chloro-3,3,3-trifluoro-1-propenyl)-2,2-dimethylcyclopropyl.

3. 5,6-Dihydro-4H-benzo[6,7]cyclohepta[1,2-b]thiophen-7-methyl 3-(2,2-dichloroethenyl)-2,2-dimethylcyclopropanecarboxylate, a compound of claim 1.

4. A compound of claim 3 which is a cis isomer.

5. The compound of claim 3 which is the 1R-cis isomer.

6. 5,6-Dihydro-4H-benzo[6,7]cyclohepta[1,2-b]thiophen-7-methyl 3-(2-chloro-3,3,3-trifluoro-1-propenyl)-2,2-dimethylcyclopropanecarboxylate, a compound of claim 1.

7. A compound of claim 6 which is a cis isomer.

8. An insecticidal or acaricidal composition comprising an admixture with an agriculturally acceptable carrier an insecticidally or acaricidally effective amount of at least one benzocycloalkanethiophenemethyl ester of the formula

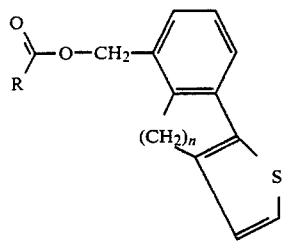

wherein n is 2 or 3 and R is selected from the group consisting of 3-(2,2-dihaloethenyl)-2,2-dimethylcyclopropyl; 3-(cyclopentylidenemethyl)-2,2-dimethylcyclopropyl; 3-(2-methyl-1-propenyl)-2,2-dimethylcyclopropyl; 3-(1,2-dibromo-2,2-dichloroethyl)-2,2-dimethylcyclopropyl; 3-(1,2,2,2-tetrabromoethyl)-2,2-dimethylcyclopropyl; 3-(2-chloro-3,3,3-trifluoro-1-propenyl)-2,2-dimethylcyclopropyl; 3-(3-chloro-2,3,3-trifluoro-1-propenyl)-2,2-dimethylcyclopropyl; 3-(2,3-dichloro-3,3-difluoro-1-propenyl)-2,2-dimethylcyclopropyl; 2,2,3,3-tetramethylcyclopropyl; 2,2-dichloro-3,3-dimethylcyclopropyl; 4-chloro-α-(1-methylethyl)phenylmethyl; 4-difluoromethoxy-α-(1-methylethyl)-phenylmethyl; 3-(1,3-butadienyl)-2,2-dimethylcyclopropyl; 2,2-dimethyl-3-(oximinomethyl)cyclopropyl; 2-(2-chloro-α,α,α-trifluoro-p-toluidino)-3-methylbutyl; 3-(2,3,4,5-tetrahydro-2-oxothien-3-ylidenemethyl)-2,2-dimethylcyclopropyl; 2,2-dichloro-1-(4-ethoxyphenyl)-cyclopropyl; 4-halo-α-(1-cyclopropyl)phenylmethyl; spiro[2,2-dimethylcyclopropane-1,1'-[1H]-indene]-3-yl; spiro[3-(2,2-dichloroethenyl)cyclopropane-1,1'-cyclohexane]-2-yl; spiro[3-(2,2-dichloroethenyl)cyclopropane-1,1'-cyclobutane]-2-yl; 3-phenyl-2,2-dimethylcyclopropyl; 3-(4-halophenyl)-2,2-dimethylcyclopropyl; 3-(4-methoxyphenyl)-2,2-dimethylcyclopropyl; 3-(4-ethoxyphenyl)-2,2-dimethylcyclopropyl; and 3-(3,4-methylenedioxyphenyl)-2,2-dimethylcyclopropyl.

9. A method of controlling insects or acarids which comprises applying to the locus where control is desired an insecticidally or acaricidally effective amount of at least one compound of the formula

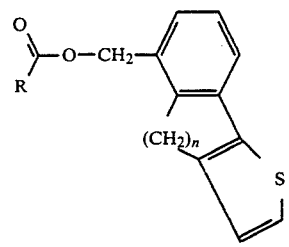

wherein n is 2 or 3 and R is selected from the group consisting of 3-(2,2-dihaloethenyl)-2,2-dimethylcyclopropyl; 3-(cyclopentylidenemethyl)-2,2-dimethylcyclopropyl; 3-(2-methyl-1-propenyl)-2,2-dimethylcyclopropyl; 3-(1,2-dibromo-2,2-dichloroethyl)-2,2-dimethylcyclopropyl; 3-(1,2,2,2-tetrabromoethyl)-2,2-dimethylcyclopropyl; 3-(2-chloro-3,3,3-trifluoro-1-propenyl)-2,2-dimethylcyclopropyl; 3-(3-chloro-2,3,3-trifluoro-1-propenyl)-2,2-dimethylcyclopropyl; 3-(2,3-dichloro-3,3-difluoro-1-propenyl)-2,2-dimethylcyclopropyl; 2,2,3,3-tetramethylcyclopropyl; 2,2-dichloro-3,3-dimethylcyclopropyl; 4-chloro-α-(1-methylethyl)phenylmethyl; 4-difluoromethoxy-α-(1-methylethyl)phenylmethyl; 3-(1,3-butadienyl)-2,2-dimethylcyclopropyl; 2,2-dimethyl-3-(oximinomethyl)-cyclopropyl; 2-(2-chloro-α,α,α-trifluoro-p-toluidino)-3-methylbutyl; 3-(2,3,4,5-tetrahydro-2-oxothien-3-ylidenemethyl)-2,2-dimethylcyclopropyl; 2,2-dichloro-1-(4-ethoxyphenyl)-cyclopropyl; 4-halo-α-(1-cyclopropyl)phenylmethyl; spiro[2,2-dimethylcyclopropane-1,1'-[1H]-indene]-3-yl; spiro[3-(2,2-dichloroethenyl)cyclopropane-1,1'-cyclohexane]-2-yl; spiro[3-(2,2-dichloroethenyl)cyclopropane-1,1'-cyclobutane]-2-yl; 3-phenyl-2,2-dimethylcyclopropyl; 3-(4-halophenyl)-2,2-dimethylcyclopropyl; 3-(4-methoxyphenyl)-2,2-dimethylcyclopropyl; 3-(4-ethoxyphenyl)-2,2-dimethylcyclopropyl; and 3-(3,4-methylenedioxyphenyl)-2,2-dimethylcyclopropyl.

* * * * *